(12) United States Patent
Franzen

(10) Patent No.: US 7,465,940 B2
(45) Date of Patent: Dec. 16, 2008

(54) IONIZATION BY DROPLET IMPACT

(75) Inventor: Jochen Franzen, Bremen (DE)

(73) Assignee: Bruker Daltonik, GmbH, Breinen (DE)

( * ) Notice: Subject to any disclaimer, the term of this patent is extended or adjusted under 35 U.S.C. 154(b) by 375 days.

(21) Appl. No.: 11/264,657

(22) Filed: Nov. 1, 2005

(65) Prior Publication Data

US 2006/0108539 A1    May 25, 2006

(30) Foreign Application Priority Data

Nov. 3, 2004   (DE) .................. 10 2004 053 064

(51) Int. Cl.
*H01J 49/42* (2006.01)
*H01J 49/00* (2006.01)
*B01D 59/44* (2006.01)

(52) U.S. Cl. .................. 250/423 R; 250/424; 250/288; 250/281; 250/282

(58) Field of Classification Search ............ 250/423 R, 250/424, 288, 281, 282
See application file for complete search history.

(56) References Cited

U.S. PATENT DOCUMENTS

| | | | |
|---|---|---|---|
| 35,413 A | 5/1862 | Sawyer | |
| 4,531,056 A | 7/1985 | Labowsky et al. | |
| 4,542,293 A | 9/1985 | Fenn et al. | |
| 5,481,107 A | 1/1996 | Takada et al. | |
| 5,504,329 A | 4/1996 | Mann et al. | |
| 5,570,988 A | 11/1996 | Gallaway et al. | |
| 5,572,035 A | 11/1996 | Franzen | |
| 5,756,994 A | 5/1998 | Bajic | |
| 5,818,041 A * | 10/1998 | Mordehai et al. | 250/281 |
| 6,107,628 A | 8/2000 | Smith et al. | |
| 6,204,500 B1 | 3/2001 | Whitehouse et al. | |

(Continued)

FOREIGN PATENT DOCUMENTS

DE   195 15 271 C2   4/1995

(Continued)

OTHER PUBLICATIONS

Aksyonov, et al., "Impact desolvation of electrosprayed microdroplets—a new ionization method for mass spectrometry of large biomolecules", Rapid Communications in Mass Spectrometry, vol. 15, John Wiley & Sons, Ltd., pp. 2001-2006, 2001.

(Continued)

*Primary Examiner*—Nikita Wells
(74) *Attorney, Agent, or Firm*—Law Offices of Paul E. Kudirka

(57) ABSTRACT

The invention relates to methods and instruments for ionizing analyte molecules, preferably biomolecules, which are dissolved in liquids or firmly adsorbed on surfaces. Liquids are nebulized at atmospheric pressure by electrospraying. Highly charged microdroplets, which enter the vacuum of the mass spectrometer through the inlet capillary, strike an impact plate when energy is fed in. The repulsive Coulomb force of the charges, the absorption of additional thermal energy and/or the conversion of their kinetic energy into thermal energy cause the microdroplets to burst and evaporate. Analyte molecules which are located in the nebulized liquid or on the impact plate are released in charged form and can be fed to the mass spectrometer for analysis by the extraction and collection effect of an ion funnel operated with RF and DC voltages.

16 Claims, 2 Drawing Sheets

U.S. PATENT DOCUMENTS

| | | |
|---|---|---|
| 6,583,408 B2 | 6/2003 | Smith et al. |
| 6,806,466 B2 * | 10/2004 | Guevremont et al. ....... 250/287 |
| 7,196,326 B2 * | 3/2007 | Franzen et al. ............. 250/288 |
| 2004/0188605 A1 | 9/2004 | Tang et al. |

FOREIGN PATENT DOCUMENTS

| WO | WO 2005/083415 A1 | 9/2005 |
|---|---|---|

OTHER PUBLICATIONS

Mahoney, et el., "Formation of Multiply Charged Ions from Large Molecules Using Massive-cluster Impact", Rapid Communications in Mass Spectrometry, vol. 8, John Wiley & Sons, Ltd., pp. 403-406, 1994.

Takäts, et el., "Mass Spectrometry Sampling under Ambient Conditions with Desorption Electrospray Ionization", Science, vol. 306, pp. 471-473, 2004.

Mahoney, et al., "Surface cleaning using energetic microcluster beams", Solid State Technology, pp. 1-8, 1998.

Takats, et al., "Mass Spectrometry Sampling Under Ambient Conditions With Desorption Electrospray Ionization", Science, Oct. 15, 2004, pp. 471-473, vol. 306.

Aksyonov, et al., "Impact Desolvation of Electrosprayed Microdroplets—A New ionization Method for Mass Spectrometry of Large Biomolecules", Rapid Communications in Mass Spectrometry, 2001; vol. 15, pp. 2001-2006.

Mahoney, et al., "Formation of Multiply Charged Ions From Large Molecules Using Massive-Cluster Impact", Rapid Communications in Mass Spectrometry, 1994, pp. 403-406, vol. 8.

* cited by examiner

IONIZATION BY DROPLET IMPACT

FIELD OF THE INVENTION

The invention relates to methods and instruments for ionizing analyte molecules, preferably biomolecules, which are dissolved in liquids or firmly adsorbed on surfaces.

BACKGROUND OF THE INVENTION

The method of electrospray ionization in ambient gas at atmospheric pressure suffers from the fact that not all the spray droplets created evaporate completely. An inlet capillary with an inside diameter of around 400 to 600 micrometers should really introduce only ambient gas with analyte ions into the mass spectrometer. It happens time and time again, however, that spray droplets enter the vacuum of the mass spectrometer through the inlet capillary and generate interfering charges somewhere in the mass spectrometer.

There is a long list of patents intended to prevent these charges developing. According to these patents, the inlet capillary must not aim directly at the through-hole for ions in the gas skimmer between the first and second pump stages (U.S. Pat. No. Re. 35,413, I. C. Mylcreest, M. E. Hail); the inlet capillary can be offset parallel to the axis of the mass spectrometer (U.S. Pat. No. 5,481,107, T. Yasuaki et al.); the inlet capillary can form an angle with the axis of the mass spectrometer (U.S. Pat. No. 5,818,041, A. Mordehai, S. E. Buttrill); the path of the ions into the vacuum system can be multiply kinked (U.S. Pat. No. 5,756,994, S. Bajic); or the spray direction can be chosen to be orthogonal to the inlet capillary so that the inertia of the droplets causes them to fly past the inlet capillary (U.S. Pat. No. 5,750,988, J. A. Apffel et al.).

The droplets cause interferences inside the mass spectrometer because their impact on instrument components in the vacuum leads to charged surfaces, and considerable efforts are made to prevent them gaining access to the mass spectrometer.

Conversely, for a decade and more, work has occasionally been carried out which generates highly charged droplets by electrospray in the vacuum of a mass spectrometer, accelerates them and fires them onto an impact plate (target), where they burst and release macromolecules in charged form. The molecules can be contained in the sprayed liquid (see for example: "Impact desolvation of electrosprayed microdroplets—a new ionization method for mass spectrometry of large biomolecules", S. A. Aksyonov and P. Williams, Rapid Communications in Mass Spectrometry, 2001; 15; 2001-2006); they can also be adsorbed on the impact plate ("Formation of multiply charged ions from large molecules using massive-cluster impact", J. F. Mahoney et al., Rapid Comm. in Mass Spectrom. 1994, 8, 403-406).

If the analyte molecules are contained in the microdroplets, the authors term this IDEM (Impact Desolvation of Electrosprayed Microdroplets); if the analyte molecules are adsorbed on a surface then the method is known as MCI (Massive Cluster Impact). The microdroplets produced in a vacuum have also been used directly to clean the surfaces of adsorbed impurities ("Surface cleaning using energetic microcluster beams", J. F. Mahoney et al., Solid State Technology, 1998, 41, 149). Electrospray ionization in a vacuum is difficult, however, and considerable effort is required to achieve a continuously operating jet of droplets. Glycerol is often used as the spray liquid.

This type of ionization and for cleaning surfaces in a vacuum using microdroplets, is made possible by electrical acceleration of the droplets, which produces a sufficiently high kinetic energy. The input of kinetic energy is necessary because evaporation causes the microdroplets in the vacuum to cool to such an extent that they can no longer evaporate by themselves. They can evaporate only when the kinetic energy is converted into thermal energy. Insufficient kinetic energy for a complete evaporation also explains the charge phenomena which are observed with electrospray ionization in the mass spectrometer if no measures are put in place to prevent microdroplets entering.

The familiar ionization of dissolved analyte substances by electrospray in ambient gas at atmospheric pressure for their mass spectrometric analysis assumes, on the other hand, that the evaporation of the spray droplets at atmospheric pressure in the ambient gas is as complete as possible. The gas is strongly heated (to a few hundred degrees Celsius) as a rule. However, evaporation can also occur in the ambient gas even without high kinetic energy and without heating the ambient gas: Highly charged microdroplets spatter even on relatively gentle contact with a surface without a high kinetic energy having to be present, as is familiar from very recent experiments with microdroplets at atmospheric pressure ("Mass Spectrometry Sampling Under Ambient Conditions with Desorption Electrospray Ionization", Z. Takats et al. Science, 2004; 306, 471-473). The microsplashes then evaporate completely, probably by absorbing thermal energy from the unheated ambient gas. This effect can be used to generate ions from analyte molecules which are adsorbed on these surfaces.

Electrospray is predominantly used in two different embodiments: normal electrospray and nanoelectrospray.

Normal electrospray operates using spray capillaries with inside diameters of between 200 and 300 micrometers and spray voltages of between four and five kilovolts. The strong electric field at the tip of the spray capillary polarizes the surface of the spray liquid, usually water mixed with organic solvents, forms the liquid surface to a so-called "Taylor cone", and pulls a jet out of its tip which resolves into fine microdroplets. Nowadays, the process is usually assisted by a spray gas, which is sharply blown in the coaxial direction. The droplets have diameters of around one micrometer and in some cases a little more. They evaporate predominantly in hot curtain gas, usually nitrogen, fed in a direction counter to that of the droplets, partly by bursting because of the Coulomb charge pressure, and partly by the evaporation of neutral particles and light ion clusters. Dissolved analyte molecules remain behind in charged form (U.S. Pat. No. 4,531,056, M. J. Labowsky, J. B. Fenn, M. Yamashita). The analyte ions can be introduced via an inlet capillary into the vacuum system of a mass spectrometer, even against a potential difference, and can be analyzed there (U.S. Pat. No. 4,542,293, J. B. Fenn et al.). Professor John B. Fenn was awarded the 2002 Nobel Prize in Chemistry for developing this method in the 1980s.

Normal electrospray has stable and unstable spray states. A stable spray state produces droplets of almost identical diameter; slightly unstable spray states, whose presence is apparent from an oscillation of the spray current, supply droplets of various diameters. The slightly unstable mode often provides a larger number of useable analyte ions, but overall, with normal electrospray, only a very small fraction of the analyte ions are ever collected through the suction cone in front of the inlet capillary and transferred to the mass spectrometer.

With nanoelectrospray, the spray capillary is thin at the tip, creating an aperture with a diameter of only approx. four micrometers (U.S. Pat. No. 5,504,329, M. Mann et al.). This electrospray ionization is operated with voltages below one kilovolt and provides microdroplets with diameters of only 100 to 200 nanometers, i.e. only around a thousandth of the volume of normal spray droplets. It is much easier to completely vaporize these microdroplets in hot nitrogen. The spray jet can be sprayed directly into the inlet capillary. Occasionally, this method also develops charges in the mass spectrometer, caused by microdroplets which are not completely vaporized. This nanoelectrospray ionization provides the most efficient utilization of the analyte molecules; no other method of ionization has been elucidated which has such a high yield of analyte molecule ions. Analyte ions are lost only in the inlet capillary.

Both methods of electrospray ionization operate according to the existing prior art with a differential pump system, in which a so-called "skimmer" is employed between the first and second pump stages. The skimmer deflects most of the gas flow, which is blown out of the inlet capillary into the first stage, in such a way that it does not decelerate and break the gas jet of the inlet capillary by direct reflection, causing the gas to back up. Only the central part of the gas jet enters the second stage of the pump system through the aperture of the skimmer; this part contains some of the ions but not sufficient to be satisfactory.

Some laboratories are now working on means of replacing the skimmer and increasing the yield of transmitted ions. The ion funnel is a successful arrangement of this type. The ion funnel operates with RF voltage in order to keep the analyte ions away from the walls of the funnel, and with DC voltage to guide them to the narrow funnel aperture (U.S. Pat. No. 6,107,628; R. D. Smith and S. A. Shaffer, also U.S. Pat. No. 5,572,035 A; J. Franzen). From there they are guided to the mass analyzer.

The ion funnel has a relatively large exit aperture, as otherwise, light ions are reflected in the ion funnel. But this allows a damagingly large amount of gas from the gas jet emerging from the inlet capillary to penetrate into the subsequent pump stages, and—in the case of existing arrangements where the mass analyzer lies precisely in the axis of the inlet capillary—the gas can continue as far as the mass analyzer. With some mass spectrometers, such as ion cyclotron resonance mass spectrometers, which only operate well with the best possible ultra-high vacuum, this gas jet is extremely damaging. The interior of the ion funnel can therefore be equipped with a "jet disturber" (U.S. Pat. No. 6,583,408 B2, R. D. Smith et al.), an impact plate which interrupts the passage of the jet into the mass analyzer. The deflected analyte ions are collected again by the surrounding ion funnel and guided to the mass analyzer.

SUMMARY OF THE INVENTION

The invention does not reject the microdroplets which penetrate the inlet capillary, but, in contrast, uses them to generate analyte ions. For this, the analyte molecules can either be entrained after being dissolved in the microdroplets, as has been the case with electrospray until now, or they can be adsorbed on sample support surfaces introduced especially for this purpose.

The invention is based on the observation that between ten and a hundred times more ions can be captured from electrospray ionization if the spray jet is aimed directly at the aperture of the inlet capillary from a short distance. In this case, however, the mass spectrometer is so contaminated within a few minutes that it can no longer operate. The invention now provides methods and devices which not only enable this increased supply of ions to be used but also (in a first embodiment) ionizes those analyte molecules which are located in the entrained microdroplets as well. The entrained microdroplets are aimed and fired at an impact plate, where they burst and generate further analyte ions. In this first embodiment, the impact plate must be strongly heated in order to facilitate the spattering (as with a hot stove plate). The ions, which then form a relatively large cloud without a rigid outline in the vacuum, have to then be removed by electrical extraction, freed of the entrained gas, and fed to the mass spectrometer, something which is achieved using a stack of diaphragms designed as an ion funnel.

The hot impact plate can be located in an ion funnel in the first stage of the vacuum pump system or, since the droplets fly straight ahead with relatively high velocity, in a second ion funnel in a second stage of the differential pump system, a large proportion of the gas being already pumped away in the first stage.

Furthermore, the invention also provides a second embodiment of methods and devices for the purpose of generating microdroplets in ambient gas virtually at atmospheric pressure, and introducing these without significant evaporation into the vacuum system of a mass spectrometer. In this second embodiment, the microdroplets are accelerated in the vacuum to a sufficiently high kinetic energy, and generate analyte ions by striking impact plates, which are designed as sample support plates and carry adsorbed analyte molecules. The analyte ions, in turn, can be extracted by ion funnels and fed to the mass spectrometer for analysis. This second embodiment can, of course, also be operated with analyte molecules in the microdroplets, which minimizes the number of analyte molecules lost through being transferred into the vacuum.

The invention thus comprises the generation of microdroplets in ambient gas virtually at atmospheric pressure, either with or without significant evaporation of the microdroplets; aspiration of the ions and microdroplets into the vacuum, with the microdroplets striking an impact plate, in which case an energy input has to be maintained to vaporize the microdroplets; and collection and transfer of the analyte ions formed into the mass analyzer of the mass spectrometer by means of an ion funnel. The energy input can be achieved by electrical acceleration of the ions or by heating the impact plate. The analyte molecules can be located in the microdroplets or adsorbed on the impact plate.

The term impact plate here shall be defined as an object of any shape onto whose surface the microdroplets impact, including, for example, an impact well or a sample support plate. The term "virtually at atmospheric pressure" should be defined as any pressure above 10,000 pascal.

BRIEF DESCRIPTION OF THE DRAWINGS

The above and further advantages of the invention may be better understood by referring to the following description in conjunction with the accompanying drawings in which.

DETAILED DESCRIPTION

Figure 4:
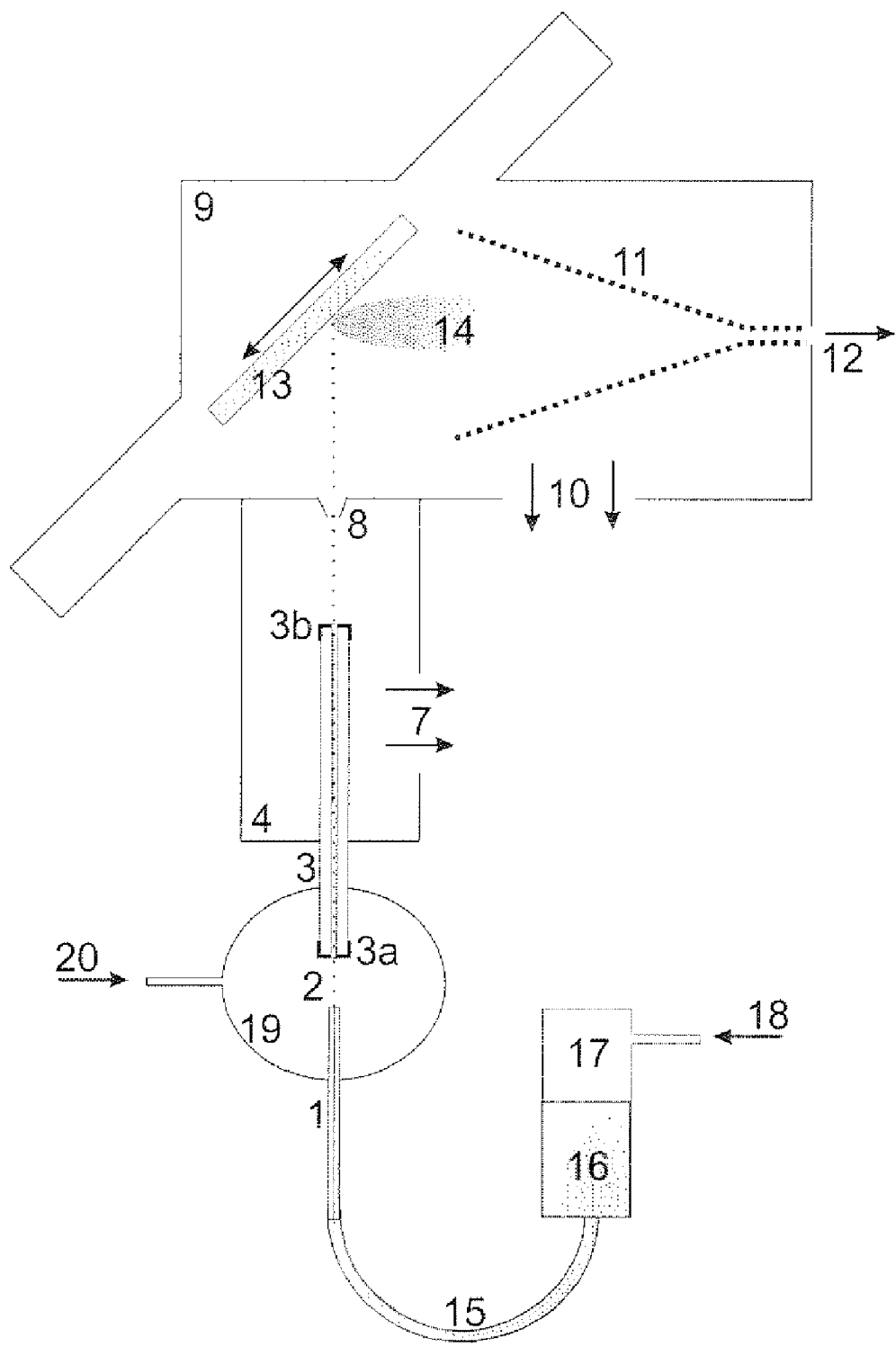
FIG. 4 reproduces a schematic outline of a device with which analyte ions are generated from analyte molecules, which are adsorbed on a movable sample support plate (13).

FIG. 4 reproduces a schematic outline of a device with which analyte ions are generated from analyte molecules, which are adsorbed on a movable sample support plate (13).

To achieve this, the spray capillary must be aligned so that it sprays through the hot ambient curtain gas flowing in a direction counter to the spray, precisely toward the admission aperture of the inlet capillary. The spraying is carried out by means of a spray voltage between the spray capillary and the inlet capillary, the inlet capillary being electrically conductive at least around the admission aperture. The separation between spray capillary and inlet capillary is selected so that the cone of spray mist in front of the admission aperture has a diameter of some four to eight millimeters at most. It is possible for the spray droplets here to largely evaporate in the hot curtain gas. The spray droplets which do not evaporate are then collected by the suction cone in front of the admission aperture of the inlet capillary and are drawn into the inlet capillary together with a large amount of hot curtain gas and a large number of previously formed analyte ions. The smaller spray droplets are further vaporized here and disappear; the larger spray droplets then enter the first pump stage of the differential pump system of the mass spectrometer and strike the impact plate. In this embodiment, the impact plate is heated in order to assist the impacting spray droplets to vaporize. The spray droplets will be termed microdroplets below. Their diameters on impact are usually much less than one micrometer.

The spray capillary can be coaxially surrounded by a further capillary, through which a spray gas is fed with high velocity to assist the spray process. It is advantageous if the spray gas is of the same type as the hot curtain gas which flows in the opposite direction, and is similarly heated. Ultrapure nitrogen is the preferred curtain gas.

The spray capillary can be connected to a liquid chromatograph; the analyte molecules of different substances, which were temporally separated from each other in the liquid chromatograph, are then fed to the mass spectrometer. However, the flow in the spray capillary should not be greater than a few hundred microliters per minute because, otherwise, the spray droplets generate too much gas in the vacuum system of the mass spectrometer. If the liquid chromatograph provides a higher eluent flow, it is advisable to split the eluent flow; since even with splitting ratios of 10:1 a considerable increase in the detection power is observed. Most of the remaining eluent flow can be utilized elsewhere, for example for loading a sample support plate with analyte molecules. The sample support plate can then be analyzed with the second embodiment of the invention described below.

The microdroplets are already accelerated in the inlet capillary by the inflowing ambient gas. Since the pressure conditions in the capillary increase the velocity of the ambient gas as the square of the distance from the entrance, the microdroplets are subjected to a permanent, accelerating friction and hence a gas-dynamic acceleration. In addition, this constantly focuses them into the axis of the capillary. The focusing is based on the Bernoulli effect. If a microdroplet leaves the axis, the parabolic velocity profile of the ambient gas in the capillary causes it to experience a higher velocity of the ambient gas toward the axis than toward the capillary wall; and the resulting lower pressure toward the axis causes it to experience a focusing force toward the capillary axis. On emerging from the inlet capillary, the microdroplets form a very fine beam of particles in the continuation of the capillary axis. The microdroplets here have velocities of between 10 and 100 meters per second.

The microdroplets then strike the impact plate, where they burst. The kinetic energy of the microdroplets and the potential energy of the repulsive Coulomb force as a result of the high charge of the droplet contribute to the bursting. Despite this, these energies are not sufficient in many cases, as can be seen from the charge phenomena in the mass spectrometer described above. The impact plate must be heated because it can cool considerably as a result of the impact of a large number of microdroplets. The impact plate becomes cold in this case, and impacting microdroplets are not able to withdraw any further thermal energy.

The impact plate here can preferably be designed in such a way that the microsplashes of the microdroplets, which splash away to the side and are accelerated by the repulsive Coulomb forces, impact again on other parts of the impact plate. This can be achieved by an indentation in the impact plate. This creates an impact well which shall, according to the definition given above, also be covered by the term "impact plate".

The vaporization of the microdroplets can be preceded by a spattering into microsplashes; the small size of the microsplashes means that their vapor pressure is then generally so high that they completely disappear within a very short time by forming analyte ions.

Figure 1:
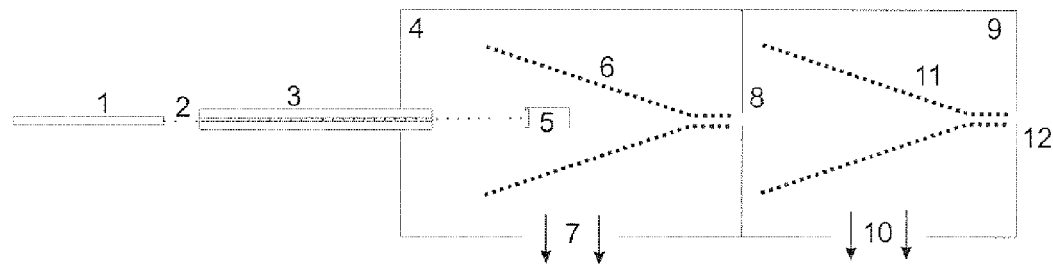
FIG. 1 illustrates a schematic array of a device according to the invention with a heated impact plate (5) in a first stage (4) of the differential pump system of a mass spectrometer (only partly shown). The spray capillary (1) close to atmospheric pressure is directed toward the inlet capillary (3), and the microdroplets of the spray jet (2) strike the heated impact plate (5) in the first pump chamber (4). The ion funnel (6) transports both the ions entering through the inlet capillary (3) as well as the ions generated by evaporation of the microdroplets into the next stage (9) of the differential pump system, where a second ion funnel (11) transports the ions in the direction (12) of the mass analyzer. The pump chambers (4) and (7) are evacuated through the pump apertures (7) and (10).

The heated impact plate (5) can be located in the middle of an ion funnel (6), for example, as schematically represented in FIG. 1. The ion funnel (6) is a stack of diaphragms made of parallel, closely packed apertured diaphragms, arranged coaxially, whose apertures taper from diaphragm to diaphragm, forming a conical inner funnel wall. The diaphragms are alternately connected to the two phases of an RF voltage; hence the wall repels ions of both polarities. The analyte ions can thus be largely freed from the ambient gas, which escapes through the spaces between the diaphragms toward a pump aperture (7). Very light ions below a cut-off mass, which is a function of the frequency, the voltage and the geometry of the apertured diaphragms, are destroyed when they hit the diaphragm surfaces, making it possible to immediately reject protons and the light ions of the liquid molecules of the microdroplets which are not of analytical interest. The ion funnel (6) is supplied not only with the RF voltage, however, but also with a DC voltage. This generates a DC voltage drop from diaphragm to diaphragm, which sucks the ions deeper and deeper into the ion funnel and transports them through the funnel exit, via the aperture (8), into a subsequent differential pump stage (9).

With normal pump systems and normal inlet capillaries (3), it is possible to maintain pressures of between 100 and 300 pascal in a first pump stage (4), and pressures of around one pascal in the second pump stage (9).

Figure 2:
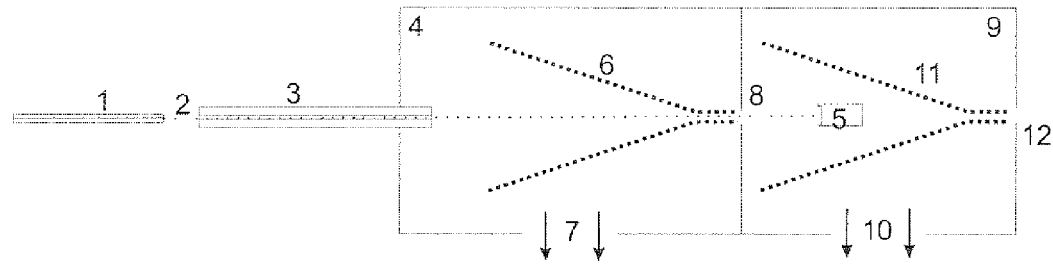
In FIG. 2, the heated impact plate (5) is located in the ion funnel (11) of the second pump stage (9).

The heated impact plate (5) can also be located in an ion funnel (11), which is located in the second differential pump stage (9), as shown schematically in FIG. 2. In the first pump stage (4) there can be a gas skimmer alone or, as in FIG. 2, a first ion funnel (6). The microdroplets fly through an aperture in the gas skimmer or through the exit of the first ion funnel (6) and meet the impact plate (5) in the ion funnel (11) of the second pump stage (9). The impact plate (5) in the ion funnel (11) of the second pump stage (9) has the advantage that the ions are generated in a chamber (9) at a better pressure, and do not run the risk (as happens in the first pump chamber (4) of being carried through the diaphragms of the ion funnel wall, (6) and on to the pump aperture (7), by the strong gas suction, at a few hundred pascal, against the repulsion of the funnel wall (6).

The ion funnels can also be constructed in a more complicated way. Ion funnels have been proposed which comprise ring quadrants, where the phases of the RF voltage are already connected to the four quadrants alternately. Other ion funnels comprise a stack of diaphragms with round diaphragms, and a subsequent stack of diaphragms with diaphragm aperture shapes which generate a quadrupole field and hence focus the ions into the axis. These altogether advantageous shapes will not be discussed further here.

Another preferred embodiment of the invention is shown schematically in FIG. 4. Here, microdroplets whose sizes are as uniform as possible are arbitrarily generated in electrospray apparatus. These microdroplets are all introduced into the vacuum system of the mass spectrometer through the inlet capillary, without being vaporized. The microdroplets here can consist of a pure solvent mixture without analyte molecules; in this case, they serve only to desorb and ionize analyte molecules from an impact plate designed as a sample support plate in the interior of the mass spectrometer. This also creates a diffuse cloud of analyte ions, which have to be captured with the help of an ion funnel and transferred to the mass analyzer in the interior of the mass spectrometer. In this case, it is advisable not to heat the impact plate, but to instead supply the required vaporization energy by electrical acceleration of the microdroplets, i.e. by increasing the kinetic energy.

This method of ionization, termed MCI (Massive Cluster Impact) for microdroplets generated in a vacuum, can be designed to be a competitive method to MALDI (Matrix Assisted Laser Desorption and Ionization). The method has the advantage that it requires neither a matrix substance nor a laser, has a much higher ion yield, and generates polycharged ions whose fragmentation is easier and more informative.

Figure 3:
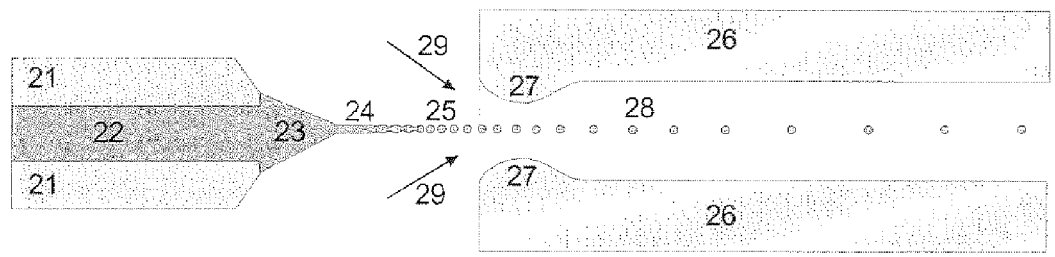
FIG. 3 is a schematic representation of a desired microdroplet formation by an electrospray apparatus in more detail. In the spray capillary (21) is the spray liquid (22), which is drawn out by the spray voltage between the spray capillary (21) and the inlet capillary (26) to form a Taylor cone (23). A fine jet of liquid (24) is drawn out of the tip of the Taylor cone (23), the jet being initially wave-shaped, due to the pulling effect of the electric field in the ambient gas (29), before resolving into a jet (25) of separate microdroplets. The sharp suction effect of the ambient gas (29) in the constriction (27) at the entrance of the inlet capillary (26) accelerates the microdroplets and resolves them into a jet (28) of widely separated microdroplets.

We will first consider how a continuous jet of microdroplets of roughly the same size can be generated. As is shown in FIG. 3, it is possible to produce a very uniform stream of microdroplets from a methanol/water mixture (22) using a spray capillary (21) extended to a tip with an aperture of some 20 micrometers in diameter, with around two kilovolts spray voltage between the spray capillary (21) and the inlet capillary (26). A slight acidification with trifluoroacetic acid (TFA) or formic acid is favorable. The methanol reduces the surface tension of the liquid and facilitates the electrospray ionization. The microdroplets (25, 28) have diameters of around 300 nanometers; they are smaller than normal spray droplets. By means of an already familiar electric circuit it is possible to prevent the jet current oscillating and hence produce microdroplets of a very uniform size. The spray capillary (21) is directed here at the input aperture of the inlet capillary (26). As curtain gas, there is a flow of moistened ultrapure nitrogen (29) at a precisely controlled temperature around the inlet capillary (26). The liquid mixture (22), the size of the spray capillary aperture (21), the temperature and the moisture content of the ultrapure nitrogen (29) can be selected so as to maintain a mode in which the highly charged microdroplets (25, 28) do not evaporate but form a continuous beam of particles (28) into the vacuum system.

At the tip of the spray capillary (21) a Taylor cone (23) is formed from whose tip a fine jet of liquid (24) is drawn out. Friction between this fine jet and the curtain gas causes the jet to resolve into fine microdroplets (25), which are accelerated in the electric field and fly very closely one behind the other. By setting the spray parameters correctly it is possible to generate around 100,000 microdroplets per second. When working in the positive mode, each microdroplet is charged with a few thousand protons; in the negative mode with a few thousand $OH^-$ groups. During a relatively long flight in ambient gas that is in moderate motion, which is not permitted here, the microdroplets would be decelerated, meaning that they would increasingly have to fly side-by-side, and Coulombic repulsion would cause them to expand to the familiar conical spray mist which drifts apart. If, on the other hand, the microdroplets are immediately drawn into the suction cone of the inlet capillary (26) because there is only a short separation between spray capillary (21) and inlet capillary (26), as shown in FIG. 3, they can continue to fly one behind the other. If, for example, there is a Laval nozzle (27) with a diameter reduced to around 300 micrometers at the entrance to the inlet capillary (which otherwise has a constant inside diameter of some 500 to 600 micrometers), then the velocity of the ambient gas (29) which is sucked in is a few meters per second. If, in the process, the microdroplets (25) take on a velocity of around one meter per second as a result of being entrained in the gas, even 100,000 microdroplets per second are all separated from each other by some ten micrometers, at diameters of 300 nanometers. The microdroplets (28) accelerated in the ambient gas in the Laval nozzle (27) therefore fly one behind the other with relatively large separations. For this mode it is therefore very favorable to have a narrowing of the inlet capillary (26) at its entrance, like a Laval nozzle.

In the inlet capillary (26) itself the microdroplets (28) are accelerated to between 10 and 100 meters per second by the ever-increasing velocity of the ambient gas. At the same time, the distances of the microdroplets (28) from each other increase continuously. In this case, the above-described focusing of the microdroplets (28) into the axis of the inlet capillary is in operation. A fine jet (28) of microdroplets is formed, which fly, cleanly separated, one behind the other, with high velocity in the axis of the inlet capillary.

After passing through the Laval nozzle (27) there is an adiabatic cooling of the ambient gas (29) and hence a possible oversaturation of the moisture content. The moisture content of the ambient gas which is fed in must therefore be adjusted so that, after this cooling, no liquid condenses on the microdroplets (28), and so that, on the other hand, the microdroplets (28) do not lose too much mass as a result of evaporation in a too dry ambient gas. Otherwise there is a danger that the microdroplets, which become labile as a result, will explode en route because of the Coulomb force.

We now turn to the schematic array in FIG. 4. The spray capillary (1) is fed here via a hose (15) from a quantity of liquid (16) in a liquid reservoir (17), a compressed gas supply (18) providing a pressure above atmospheric in the reservoir. The pressure and the capillary forces in the spray capillary (1) ensure that the correct quantity of spray liquid is supplied. A spray voltage between the spray capillary (1) and the metal end cap (3a) of the inlet capillary (3) produces the spray jet (2), the details of which can be seen in FIG. 3. The nebulization takes place at atmospheric pressure in a chamber (19) charged with temperature- and moisture-regulated ambient gas, preferably nitrogen.

Highly charged microdroplets can attain a labile state if they evaporate to such an extent that Coulombic repulsion of the charges, which are uniformly distributed over the spherical surface, roughly cancels out the surface tension. The slightest deformation of the sphere then leads to constriction and almost explosive division of the microdroplet into two or more smaller microdroplets. This labile state can be avoided by regulating the moisture of the ambient gas. If, on the other hand, the density of the charges on the surface is too low, the ionization process on impact is more difficult because insufficient potential repulsion energy is available to vaporize the microsplashes.

The inlet capillary (3) can be made wholly of metal, but here it is made of insulating material, for example glass. In this case, the inlet capillary (3) is equipped with two metal end caps (3a) and (3b), which can be set at separate potentials. In the insulating inlet capillary (3) the ions and microdroplets can be pushed against a potential difference toward a potential which is several kilovolts higher, the friction of the gas acting as the transporting force (U.S. Pat. No. 4,542,293, J. B. Fenn et al.). It is favorable if the glass capillary (3) in the interior is coated with a resistance material so that a longitudinal resistance of around $10^9$ ohms is created (DE 195 15 271 C2, J. Franzen, corresponding to U.S. Pat. No. 5,736,740 A). The entrained ions which impact on the wall of the inlet capillary can then be discharged without the surface becoming charged.

An opposing potential in the inlet capillary reduces the velocity of the emerging microdroplets. They then definitely require a strong postacceleration. Conversely, the counterpotential increases the focusing of the microdroplets in the axis of the inlet capillary. A compromise must be found by experiment here.

As schematically shown in FIG. 4, this fine, well-focused jet of multiply charged and well-accelerated microdroplets (2) can be used for the ionizing desorption of substances which are adsorbed in small sample areas on a movable sample support plate (13). The velocity of the microdroplets and the strong charge cause the microdroplets to explode into many small microsplashes on impact on the sample support plate (13). In the process, they take up adsorbed molecules, which then remain behind as an ion cloud (14) after the rapid, complete evaporation of the microsplashes. The minuscule dimensions of the microsplashes mean that they have a greatly increased vapor pressure. If complete evaporation occurs, multiply charged ions are also created in the ion cloud (14) in addition to singly charged ones, the former being particularly suitable for fragmentations and hence for examining the structures of the molecules.

The process upon impact of the microdroplets can be controlled to a large degree by the velocity of the microdroplets (2). To control the velocity, the microdroplets (2) are subjected to a postacceleration on leaving the inlet capillary. This postacceleration is achieved by applying a postacceleration voltage of up to a few kilovolts between the end (3b) of the inlet capillary (3) and a gas skimmer (8), which forms the aperture from the first pump stage (4) to the next pump stage (9). A gas discharge can be prevented by shaping the chamber (4). Both the gas skimmer (8) and the sample support plate (13) can be at ground potential, for example, the potential for accelerating the microdroplets being applied only to the metal end (3b) of the inlet capillary (3). The sample support plate (13) here is preferably located downstream of the gas skimmer (8), in the second stage (9) of the differential pump system.

The acceleration of the microdroplets can also take place somewhere else en route to the sample support plate, however.

The analyte ions, which are generated in front of the sample support plate (13), form an ion cloud without clear-cut boundaries (14), which has to be fed to the mass analyzer. According to the invention, the ion funnel (11) serves this purpose, its function having already been described in more detail above. The ion funnel (11) gently guides the ions of the ion cloud (14) to the narrow exit end of the funnel, and sends them in the direction (12) of the mass analyzer.

The yield of analyte ions is extraordinarily high, several orders of magnitude higher than the yield of an ionization by matrix-assisted laser desorption (MALDI) in a vacuum. A further advantage compared with MALDI consists in the fact that the jet of microdroplets, especially from adsorbed biomolecules, also generates multiply charged ions (as is the case with electrospray ionization) whose fragmentation in suitable mass spectrometers is much better and more informative than the predominantly singly charged MALDI ions. The fragmentation can thus be achieved using the familiar methods, such as collisionally induced decomposition at low or high collision energies, electron capture, electron transfer reactions or others.

A microdroplet with its thousands of protons can generate a large number of positively charged analyte ions when it impacts on the sample support plate (13). There are reports in the literature indicating that a microdroplet 300 nanometers in diameter can sweep a surface area around 300 nanometers in diameter completely clean of adsorbed analyte molecules, if the occupancy is not overly high, and largely ionizes the analyte molecules which are desorbed. In negative mode it is then possible to generate negatively charged analyte ions with the then negatively charged microdroplets.

The lowest concentrations of peptides that, with care and rapid working, can be handled without large losses at the vessel and pipette walls are around ten femtomols per microliter. Applying a microliter of this solution to a sample area of one square millimeter produces a layer of adsorbed peptides, after the solvent has dried, which corresponds to one hundredth of a monomolecular coating. The layer thus consists of isolated peptide molecules adsorbed on the surface even though there is a total of some six billion peptide molecules on the square millimeter. In the impact region of a microdroplet measuring some 300 nanometers in diameter, there are 600 peptide molecules, most of which become ionized. Assuming an ion yield here of only ten percent, then one obtains around 60 ions per microdroplet; with 100,000 microdroplets per second, around six million ions per second are obtained. If careful scanning of the sample region could enable all the microdroplets to be placed side-by-side and very close together, it would be possible to maintain this extremely large analytical current of ions for longer than 100 seconds.

Slightly smaller ion currents are obtained when only 10,000 microdroplets per second are generated, but with diameters of between 500 and 600 nanometers.

A very good mass spectrum requires only a few hundred up to a maximum of 10,000 ions, depending on how signal-intensive the mass spectrum is. From these ten femtomols of peptide molecules, an ion current is thus obtained with which hundreds of mass spectra can be scanned, even if considerable ion losses occur. With this ion current it is possible to scan large numbers of fragment ion spectra in suitable mass spectrometers, even though larger numbers of analyte ions are required for fragment ion spectra. The detection limit will presumably lie at a few attomoles or even much lower; it depends essentially on impurities whose signal noise interferes with the ion measurement. The low detection limit is particularly valuable for mixture analyses.

Since this method requires no matrix molecules to assist the desorption, the mass spectrum is much less polluted by the chemical noise of the matrix substance, which generally forms numerous cluster ions and fragments thereof in the laser plasma. The mass spectrum therefore has much less chemical noise interference than MALDI mass spectra. For this reason alone the detection limits for this method are considerably lower than with MALDI.

For higher analyte concentrations it can also be advantageous in the method according to the invention to dilute and isolate the analyte molecules by also applying matrix substances so that the analyte molecules cannot be ionized as clusters. It is also possible to use types of matrix substances which are quite different to those used for MALDI, because they do not have to be available either for absorbing the laser energy or for the protonation of the analyte molecules. Substances with very low molecular weights, in particular, are advantageous here, since their ions can be rejected in the ion funnel because they lie below the mass threshold.

In contrast to MALDI, where the sample support plate must be extremely flat and precisely formed, this method does not require it to be flat. The sample area can even be rough or have a microstructure. For example, in the sample area, microbeads can be positioned, on the surface of which the analyte molecules are adsorbed. Microbeads make it possible to handle very small sample quantities with low losses. The sample support plate (13) can even be manufactured of electrically insulating material, for example polytetrafluoroethylene (PTFE), or from metal with electrically insulating surface coatings.

The ions generated by the bursting of the microdroplets fly apart in all directions because of their Coulombic repulsion, and also the bursting process itself. They have to be collected again and concentrated. The use of an ion funnel (11) is therefore an essential basic component of the invention.

All types of mass spectrometer can, in principle, be used to analyze the ions of the ion beam (12). There are, however, particularly favorable types of mass spectrometer, for example ion cyclotron resonance spectrometers for particularly accurate determination of the ion mass, with accuracies better than one millionth of the mass, or RF quadrupole ion traps for analyzing the structure of the analyte molecules by the formation of granddaughter and great-granddaughter ions.

Especially favorable, however, are reflector time-of-flight mass spectrometers with orthogonal ion injection, because they combine a very good mass accuracy (a few millionths of the mass) with a high dynamic range of measurement and very rapid scanning, and have a relatively small configuration. Some of these time-of-flight mass spectrometers are equipped with devices for selecting parent ions and fragmenting these parent ions into daughter ions, which can be used to study the structure of the analyte ions.

The apparatus described here in FIG. 4 can particularly be used in the analysis of proteins. It is possible, for example, to use this apparatus to identify individual proteins which have been separated by 2D gel electrophoresis and individually digested to digest peptides by enzymes such as trypsin, and to analyze them for deviations and modifications. To achieve this, the digest peptide mixture is applied in solution to a sample area of the sample support plate (13). After drying the sample, the sample support plate is introduced into the apparatus shown in FIG. 4 through a lock (not shown) and aligned using the movement device of the sample support plate so that the jet of microdroplets impacts exactly on the coated sample area. The ions of the digest peptides produce a mass spectrum which enables the mass of each individual digest peptide to be very accurately determined. Mass accuracies of the order of a few millionths of the mass (ppm), or less, can be achieved, which enables very unambiguous identification by searching in protein data bases. If deviations for individual digest peptides occur, the ions of these digest peptides can be fragmented. The mass spectra of the fragment ions then make it possible to detect mutative changes or posttranslational modifications. De novo sequencing is also possible if no other knowledge about the protein is available.

If the sample support plate (13) is the size of a microtitration plate, it is easy to define 384 or even 1536 individual sample areas on it since, as described above, even very small sample areas of around only one square millimeter are sufficient to analyze the analyte ions. The individual sample areas can each be surrounded by a milled ring channel which prevents the sample solution spreading out.

We will not go into further application methods and further designs of the device according to the invention here. With knowledge of the basic invention it is possible for those skilled in the art to easily make further designs of the method and device. All these designs are intended to be included here.

What is claimed is:

1. Device for the ionization of analyte molecules for their analysis in a mass spectrometer, wherein
    (a) an inlet capillary begins virtually at atmospheric pressure and ends in the first stage of a differential pump system of the mass spectrometer,
    (b) an electrospray capillary virtually at atmospheric pressure directed at the input aperture of the inlet capillary,
    (c) an impact plate arranged in the vacuum in the axial direction of the inlet capillary,
    (d) a device to supply energy for the vaporization of the microdroplets, and
    (e) an ion funnel located in the vacuum in the immediate vicinity of the impact plate, to collect the ions and transmit them to the mass analyzer of the mass spectrometer.

2. Device according to claim 1, wherein energy to vaporize the microdroplets is supplied by heating the impact plate.

3. Device according to claim 1, wherein energy to vaporize the microdroplets is supplied by electrical acceleration of the charged microdroplets in the vacuum.

4. Device according to claim 1 to 3, wherein the analyte molecules are located in the microdroplets.

5. Device according to claim 1 to 3, wherein the analyte molecules are located on the impact plate.

6. Device according to claim 1 to 5, wherein the entrance of the inlet capillary has a constriction similar to a Laval nozzle.

7. Device according to claim 1 to 6, wherein the spray capillary is positioned coaxially to the inlet capillary.

8. Device according to claim 1 to 7, wherein there is a device to supply moistened, temperature-controlled ambient gas between spray capillary and inlet capillary.

9. Device according to claim 8, wherein there is a device to regulate or control the temperature and the humidity of the ambient gas.

10. Device according to claim 3 to 9, wherein the impact plate is designed as a sample support plate whose surface can be loaded with analyte molecules.

11. Device according to claim 10, wherein the sample support plate has sample areas separated from each other, each of which can be loaded with analyte molecules.

12. Device according to claim 10 to 11, wherein the sample support plate can be moved parallel to its surface.

13. Device according to claim 10 to 12, wherein the sample support plate is the size of a microtitration plate.

14. Device according to claim 1 to 2, wherein the impact plate is located in an ion funnel.

15. Method of ionizing analyte molecules, comprising the following steps:
   (a) Generation highly charged spray droplets virtually at atmospheric pressure by electrospray in an ambient gas,
   (b) Transfer of spray droplets together with ambient gas through an inlet capillary into the vacuum system of a mass spectrometer,
   (c) Acceleration of the spray droplets in an electric field,
   (d) Impact of the spray droplets on an impact plate, where analyte molecules dissolved in the spray droplets or adsorbed on the impact plate are released in ionized form as analyte ions when the spray droplets burst,
   (e) Collection of the analyte ions and separation from the ambient gas by an ion funnel, and
   (f) Analysis of the analyte ions in the mass analyzer of the mass spectrometer.

16. Method of ionizing analyte molecules, comprising the following steps:
   (a) Generation of highly charged spray droplets by electrospray of a spray liquid in which analyte molecules are dissolved virtually at atmospheric pressure in a ambient gas,
   (b) Transfer of spray droplets together with ambient gas and previously formed analyte ions through an inlet capillary into the vacuum system of a mass spectrometer,
   (c) Impact of the spray droplets onto a heated impact plate, where analyte molecules dissolved in the spray droplets are released in ionized form as analyte ions when the spray droplets burst,
   (e) Collection of the analyte ions and separation from the ambient gas by an ion funnel, and
   (f) Analysis of the analyte ions in the mass analyzer of the mass spectrometer.

* * * * *